(12) United States Patent
Harms et al.

(10) Patent No.: US 9,029,635 B2
(45) Date of Patent: May 12, 2015

(54) METHOD FOR INCREASING SUCROSE YIELD IN AGRICULTURAL PRODUCTION OF SUGAR BEET AND SUGAR CANE

(75) Inventors: Karsten Harms, Worms (DE); Britta Schulz, Einbeck (DE)

(73) Assignees: KWS Saat AG, Einebeck (DE); Suedzucker AG Mannheim/Ochsenfurt, Mannheim (DE)

( * ) Notice: Subject to any disclaimer, the term of this patent is extended or adjusted under 35 U.S.C. 154(b) by 138 days.

(21) Appl. No.: 13/133,178

(22) PCT Filed: Dec. 18, 2009

(86) PCT No.: PCT/DE2009/001797
§ 371 (c)(1),
(2), (4) Date: Jun. 7, 2011

(87) PCT Pub. No.: WO2010/072210
PCT Pub. Date: Jan. 7, 2010

(65) Prior Publication Data
US 2011/0239536 A1    Oct. 6, 2011

(30) Foreign Application Priority Data
Dec. 22, 2008 (DE) .......................... 10 2008 064 184

(51) Int. Cl.
*C12N 15/82* (2006.01)

(52) U.S. Cl.
CPC ........ *C12N 15/8261* (2013.01); *C12N 15/8246* (2013.01)

(58) Field of Classification Search
None
See application file for complete search history.

(56) References Cited

U.S. PATENT DOCUMENTS 6,384,300 B1 *  5/2002  Rausch et al. ................. 800/284
6,713,666 B2 *  3/2004  Helentjaris et al. ......... 800/320.1

OTHER PUBLICATIONS

Rausch et al, 2004, Biochimica et Biophysica Acta, 1696:253-261.*
Greiner et al, 1999, Nat Biotech., 17:708-711.*
Sévenier et al, 2002, J. Am. College of Nutrition, 21:199S-204S.*
Greiner, S. et al. "Cloning of a Tobacco Apoplasmic Invertase Inhibitor" Botanisches Institute, Heidelberg, Germany Plant Physiol. (1998), vol. 116, pp. 733-742.
Link, M. et al. "In *Arabidopsis thaliana*, the invertase inhibitors AtC/VIF1 and 2 exhibit distinct target enzyme specificities and expression profiles" Heidelberg Institute of Plant Sciences (HIP), Heidelberg, Germany FEBS Letters 573 (2004), pp. 105-109.
Fire, A. et al. "Potent and specific genetic interference by double-stranded RNA in *Caenorhabditis elegans*" Carnegie Institution of Washington, Department of Embryology, Baltimore, Maryland Nature, vol. 391, Feb. 19, 1998, pp. 806-811.
Bate, N.J. et al. "An Invertase Inhibitor from Maize Localizes to the Embryo Surrounding Region during Early Kernel Development" Agronomic Traits, Trait and Technology Development, Johnston, Iowa Plant Physiology, Jan. 2004, vol. 134, pp. 246-254 www.plantphysiol.org © American Society of Plant Biologists.
Eamens, A. et al. "RNA Silencing in Plants: Yesterday, Today, and Tomorrow" Commonwealth Scientific and Industrial Research Organization Plant Industry, and University of Sydney, Australia Plant Physiology, Jun. 2008, vol. 147, pp. 456-468, www. plantphysiol.org © 2004 American Society of Plant Biologists.
Watson, J. et al. "RNA Silencing Platforms in Plants" CSIRO Plant Industry, Australia FEBS Letters 579, (2005) pp. 5982-5987.

* cited by examiner

*Primary Examiner* — Ashwin Mehta
*Assistant Examiner* — Jason Deveau Rosen
(74) *Attorney, Agent, or Firm* — Novak Druce Connolly Bove + Quigg LLP

(57) ABSTRACT

A nucleic acid suitable for reducing the enzymatic activity of an invertase for configuring a sucrose storage organ of a plant, wherein the sucrose concentration is increased relative to the sucrose concentration of an unchanged control sucrose storage organ of the same genotype at a comparable stage of development. The increase in sucrose concentration by X percentage points can thereby lead to a changed or unchanged sucrose storage organ yield, wherein, in the case of a reduction in the sucrose storage organ yield, the reduction is a maximum of 5X percent. The invention further relates to a method for increasing the sucrose yield in agricultural production of sugar beet or sugar cane plants, wherein sugar beet or sugar cane plants are used, the genetic makeup thereof being set up for reducing the enzymatic activity of an invertase.

6 Claims, 2 Drawing Sheets

Figure 1:
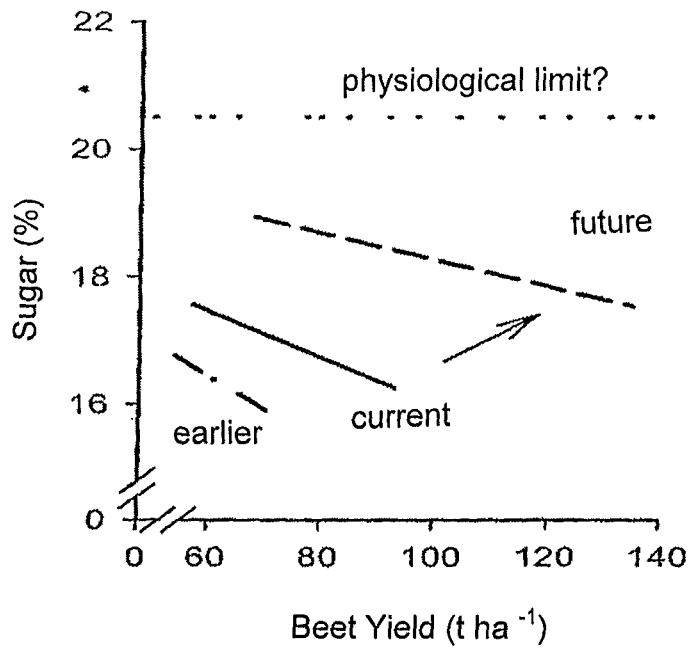

SEQUENCE LISTING

<160> NUMBER OF SEQ ID NOS: 2

<210> SEQ ID NO 1
<211> LENGTH: 811
<212> TYPE: DNA
<213> ORGANISM: Nicotiana tabacum

<400> SEQUENCE: 1
cggcacgaga acaaaaccaa acacctttcc tttggcctct cctccttta tcttttatat    60

```
caatcctcat cttcaataac accactctca aaacaaatga gaaacttatt ccccatattt      120
atgttaatca ccaatctagc attcaacgac aacaacaaca gtaataatat catcaacacg      180
acctgcagag ccaccacaaa ctaccccttg tgcctcacca ccctccactc tgatccccgt      240
acctccgagg ccgaggggc ggacctcacc accctcggcc tcgtcatggt agatgcggta       300
aaattaaagt ccatcgaaat aatgaaaagt ataaaaaaac tcgaaaaatc gaaccccgag      360
ttgagactac ctcttagcca atgttacata gtgtattatg ctgttctaca tgctgatgta      420
actgttgctg ttgaagcttt aaaaagagga gtccctaaat ttgctgaaaa tggaatggtt      480
gatgttgctg tagaagcaga aacttgtgag tttagtttta agtataatgg attggtttct      540
ccagtttctg atatgaataa ggagattatt gaactgtctt ctgtggctaa atctattatt      600
agaatgctat tatgaggaaa ttaaagaacc aaagatacaa ggttctggtt atgttagttt      660
attagtgctg taataggatt tttatattcc tgtgtttttt ttgcttttt  tatttcattt      720 gggtgcttgt gtgtatatgt gaaaatgagt gtgaattatg tcaaacataa acatagatta      780
gaaattactc ctgaaaaaaa aaaaaaaaaa a                                    811

<210> SEQ ID NO 2
<211> LENGTH: 555
<212> TYPE: DNA
<213> ORGANISM: Beta vulgaris

<400> SEQUENCE: 2
atgacaactc taaacacctc tttaccacat cttcacctcc tcttcattac ccttcttaca       60
ctattcacca cctctacttt agcgtattct cgcaagacca ccaacgacct tgtaaccacc      120
acgtgcaagc aaacacccga cccgattctt tgcgaagctt cgctccgatc agactctcgg      180
agctccaagg ctgctgactc tgaaggttta atcctgatca tgatcgacgt tgtcaaaact      240
cggttttcgg actcgtttcg atatgtagag gacttgaccc ggaagaccca tgacccggat      300
gtaatccggg ccctgcaaga gtgtaagcaa ctctatcggg ttgtgttaga tgtaagtgta      360
ggtttagcag tgagagcagt aaagcaaggg gatccgaaat tcggggagca agctatggtg      420
gatgcgggta atgaggccga ggggtgtcgg atggcgttcc cggaaggtaa ggttccgggt      480 ggatcgtgg gtcgaacacg gatgctccat ggagtatcta atgtggctgc ttctatgatt       540
aagagtttgg aatga                                                      555
```

METHOD FOR INCREASING SUCROSE YIELD IN AGRICULTURAL PRODUCTION OF SUGAR BEET AND SUGAR CANE

The present invention relates to the use of a nucleic acid, which is able to reduce the enzymatic activity of an invertase in a plant cell, as well as a method for increasing the sucrose yield in agricultural cultivation of sugar beet and sugar cane.

Sugar beets are biennial plants. Vegetative growth takes place in the first year of development, wherein the plant develops a rosette of leaves and forms a primary root, the taproot. In the second year, the generative phase, inflorescence and seeds are formed. A special feature of the physiology of sugar beet yield is that the accumulation and storage of sucrose occurs predominantly in the first vegetation year. For production of sucrose, sugar beets will therefore be harvested in the vegetative stage of development.

Decades of efforts in sugar beet breeding have brought remarkable increases in terms of taproot yield as well as sucrose yield. Nevertheless, these increases are still not satisfactory, although the sucrose concentration of the taproot today is about 15-20% of the beet's fresh weight.

From EP 0956357 B1 the use of a nucleic acid is known, that codes for a polypeptide able to reduce the enzymatic activity for an invertase, for producing a transgenic plant with reduced storage-associated sucrose loss. This document does not provide any indication of the ability to use of an invertase to increase the sucrose concentration in a sucrose storage organ of a plant.

Beyond this, EP 1346054 B1 discloses the inhibition of plant vacuolar invertase. This document likewise only describes an improved storage stability of plants, and no increase in sucrose concentration.

It is therefore an object of the present invention to further increase the sucrose concentration in a sucrose storage organ of a plant. In particular, the object of the present invention is to provide a method for agricultural cultivation of sugar beet and sugar cane, with which the sucrose yield can be increased.

In accordance with the invention, the solution to the problem lies in the use of a nucleic acid, able to reduce the enzymatic activity of invertase in a plant cell, to form a sucrose storage organ of a plant in which the sucrose concentration is increased compared with the sucrose concentration of a non-GM control sucrose storage organ of the same genotype in a comparable developmental stage.

So far, however, sucrose concentration and taproot yield have been negatively or inversely correlated, i.e., varieties with high sucrose concentration produce lower taproot yield than varieties with lower sucrose concentration. The reason for this is that sugar beets with a high sucrose concentration form rather small taproots.

An attempt to explain the negative relationship between sucrose concentration and taproot yield in sugar beets was made in 1973 by Milford. Here, a correlation was made between beet weight and the size of the parenchymatous storage cells. Large parenchyma cells accordingly have a lower sucrose concentration than small parenchyma cells.

The relationship between sucrose concentration and taproot yield remains negative even in new varieties, though not as tightly correlated as it was described earlier (Campbell and Kern 1983, Hoffmann and Märänder 2002). The advances in cultivation methods thus far have resulted only in a shift of the negative relationship between sucrose concentration and taproot yield, but not to a fundamental change in this relationship (FIG. 1).

The above-described negative relationship between sucrose concentration and sucrose storage organ yield for sugar beet is essentially true also for sugar cane.

Surprisingly, it was now been found that with the novel use of a nucleic acid, which is useful in a plant cell to reduce the enzymatic activity of invertase, the negative or inverse correlation between sucrose concentration and sucrose storage organ yield (sugar beet taproot yield or sugar cane yield) can be reduced or eliminated.

In particular, the inventive use of the nucleic acid can, in the case of an increase in sucrose concentration by X percentage points, leads to a reduction of sucrose storage organ yield, wherein the reduction of sucrose storage organ yield is a maximum of 5 X percent.

According to a particular embodiment of the invention, with the use of nucleic acid which is useful in a plant cell to reduce the enzymatic activity of invertase, the sucrose storage organ yield is unchanged or increased.

Thus, the increase of sucrose concentration, for example by 2 percentage points, leads, in the event of a reduction of sucrose storage organ yield, to a reduction of maximally 10 percent. In general however, the increase in sucrose concentration also leads to an increase in sucrose storage organ yield, so that the sucrose concentration of the sucrose storage organ is not negatively correlated with the sucrose storage organ yield.

In the case of sugar beet, the sucrose concentration indicates the amount of sucrose in the taproots' fresh weight, namely in percent. The term "taproot yield" is understood to be with reference to the fresh weight of floating, optimally trimmed beet. From the taproot yield, multiplied by the sucrose concentration, the sucrose yield is obtained.

Also, using the example of sugar beet, the advantage of the present invention is illustrated below on the basis of a sample calculation.

A particularly suitable nucleic acid to reduce the enzymatic activity of invertase is a nucleic acid that encodes an invertase inhibitor. Invertase inhibitors were first described in potatoes (Schwimmer et al. 1961). They are known from sugar beet, tomato and tobacco (Pressey 1968, Pressey 1994, Weil et al. 1994, Rausch and Greiner 2004). However, although invertase inhibitors are known in the art, it was surprising that the sucrose concentration of a sugar beet taproot can be increased by means of these polypeptides. In particular, it was not known, that thereby the negative relationship between sucrose concentration and sucrose storage organ yield could be caused to subside.

On the other hand, the availability of various invertase inhibitors offers also a good basis for this new use. Thus, the nucleic acids which encode polypeptides for a reduction of the enzymatic activity of invertase can be easily obtained or identified and used in sugar beet and sugar cane, namely by breeding techniques as well as by genetic engineering.

Another way to reduce the enzymatic activity of invertase can be achieved by the fact that the enzymatic activity of invertase is not reduced by inhibiting a polypeptide, but rather, for example, using antisense RNA or RNA interference. Both methods are now among well-known standard techniques. In the case of antisense RNA, a single-stranded RNA is used that is complementary to the m-RNA of the invertase. By subsequent pairing of the complementary RNAs, there is an inhibition of translation of the mRNA, thus preventing the genetic expression of invertase in the cell. RNA interference, in contrast, uses an inverted repeat of a cDNA fragment, which forms after transcription a double-stranded RNA molecule that is cleaved by the plant's own enzymes into fragments with a length of about 21 to 23 nucleotides, which lead to a translational blockade of the m-RNA of the invertase.

Invertases from sugar beet are also known (Rosenkranz et al, 2001, Gonzales et al, 2005), or can be isolated without much difficulty on the basis of known invertases (Sturm and Chrispeels, 1990; Sturm, 1999) from sugar beet and sugar cane, so that also corresponding antisense RNA or RNA interference constructs are readily produced. Using well-known plant transformation methods, such constructs can be easily transferred to plants where they can be expressed.

According to another preferred embodiment of the invention, the nucleic acid is a heterologous nucleic acid derived from *Nicotiana tabacum*.

The term "heterologous" means that the nucleic acid in question, with respect to the host cell, has another source or is at least in an unnatural state. If a host cell is transformed with a nucleic acid derived from a foreign organism, the nucleic acid sequence is heterologous to the host cell and the progeny of the host cell, who carry said nucleic acid sequence.

Surprisingly, with transgenic starting points, increased sucrose concentrations could be detected only in taproots of transgenic progeny of primary transformants grown from seeds. The beet weights were unchanged compared to non-transgenic control, resulting in an increased sucrose yield. In adventitious roots, i.e., taproot-like structures that are formed directly from the primary transformants, no change in sucrose concentration was observed.

According to another preferred embodiment of the invention, the heterologous nucleic acid is a sequence according to SEQ ID NO: 1 or a nucleic acid sequence with a sequence complementary to the sequence shown in SEQ ID NO: 1 or can hybridize with segments thereof.

As used herein, "hybridize" shall refer to hybridizing under normal conditions, as described in Sambrook et al. (1989), preferably under stringent conditions. Stringent hybridization conditions include: hybridization in 4×SSC at 65° C., followed by repeated washing in 0.1×SSC at 65° C. for a total of about 1 hour. Low stringency hybridization conditions include for example: hybridization in 4×SSC at 37° C., followed by repeated washing in 1×SSC at room temperature. "Stringent hybridization conditions" can also mean: hybridizing at 68° C. in 0.25 M sodium phosphate, pH 7.2, 7% SDS, 1 mM EDTA and 1% BSA for 16 hours and then washing twice with 2×SSC and 0.1% SDS at 68° C.

The polypeptide coded by the nucleic acid, the invertase inhibitor, is after transformation in a sugar beet or cane cell preferably localized vacuolar, in the cytosol or in the cell wall.

In a further embodiment of the invention, the nucleic acid is a homologous nucleic acid. The term "homologous" in this context means that the nucleic acid is derived from the same natural source as the host cell. The term "homologous" also refers to a nucleic acid sequence that is introduced into the same natural original cell type from which it originated, but is, for example, under control of another regulatory element not naturally occurring in this cell type or in this combination. Therein, regulatory elements are sequences that are involved in supporting the expression of a nucleotide sequence. They include for example promoter and terminator sequences. Thus, a host cell may for example be transformed with a nucleic acid from a same type organism to achieve, for example, over-expression of this nucleic acid.

On the other hand, it is possible to increase by known breeding methods the expression of the nucleic acid in cells or to ensure that the activity of the encoded polypeptide is enhanced in the cells. For example, the allelic variation at the genetic locus of the invertase from sugar beet and sugar cane can be analyzed and then work in breeding can continue with the best allele. The basis for this may be, in the case of sugar beet, the sequence of the invertase inhibitor BvC/VIF1 (*Beta vulgaris* cell wall or vacuolar inhibitor of beta-fructosidase) according to SEQ ID NO: 2 as well as a nucleic acid sequence that can hybridize with a sequence complementary to the sequence shown in SEQ ID NO: 2 or portions thereof.

The analysis of allelic variation occurs in the manner that first of all, by comparative sequencing, the gene locus of the invertase inhibitor, which resides in a population of existing alleles, is identified. Then the different alleles are stored by repeated back-crossing always with the same genetic background. The resulting near-isogenic lines are analyzed for expression of the invertase inhibitor. The analysis is performed by a Northern Blot Technique or RT-PCR.

A comparison of the effectiveness of the different alleles of the invertase inhibitor can also be measured indirectly through the activity of the invertase enzyme.

Near-isogenic sugar beet lines are grown in a field experiment. After the harvest, beet yield and sucrose concentration are determined. This allows a comparison of the alleles in relation to the target feature—sucrose yield. The allele with the best effect with respect to sucrose yield is then crossed into the current breeding material and is used for variety development.

The present invention also relates to a method for increasing the sucrose yield in agricultural cultivation of sugar beet and sugar cane. Here, sugar beet or sugar cane plants are used of which the genetic makeup is directed towards the reduction of the enzymatic activity of invertase.

The genetic composition of the beet or cane plant can be made by genetic engineering or conventional plant breeding methods. In this respect, reference is made to the above-mentioned possibilities for the new use of a nucleic acid.

A preferred embodiment of the inventive method provides that the genetic makeup allows the formation of a sucrose storage organ, in which the sucrose concentration is not negatively correlated with the sucrose storage organ yield.

The following calculation illustrates, using sugar beet as an example, how the new procedure has an overall effect on the total sucrose yield.

The sucrose yield of a standard sugar beet variety is, in the case of a beet yield of 60 t/ha and a sucrose concentration of the root of 17%, a total of 10.2 t/ha. With the inventive method however sucrose concentrations of 18% or more can be achieved. With the same beet yield a 1% increase in concentration is already a sucrose yield increase of 600 kg of sucrose per hectare. Because of the previously negative correlation between sucrose concentration and beet yield, so far increases in sucrose concentration, for example going from 17% to 18%, have led to an overproportional reduction in beet yield, so that an increase in concentration of sucrose concentration is only of very limited use.

The invention is further illustrated in the following by the figures and a preferred embodiment.

FIG. 1 shows the advances in breeding in beet yield and sucrose concentration in sugar beet varieties according to Hoffmann 2006. According to the graphic, a high sucrose concentration is only achieved at a relatively low taproot yield. A high taproot yield is associated with a relatively low sucrose concentration. By breeding progress, the slope of the regression line indeed decreases further, but the relationship between taproot yield and sucrose concentration remains negative in new varieties.

Figure 2:
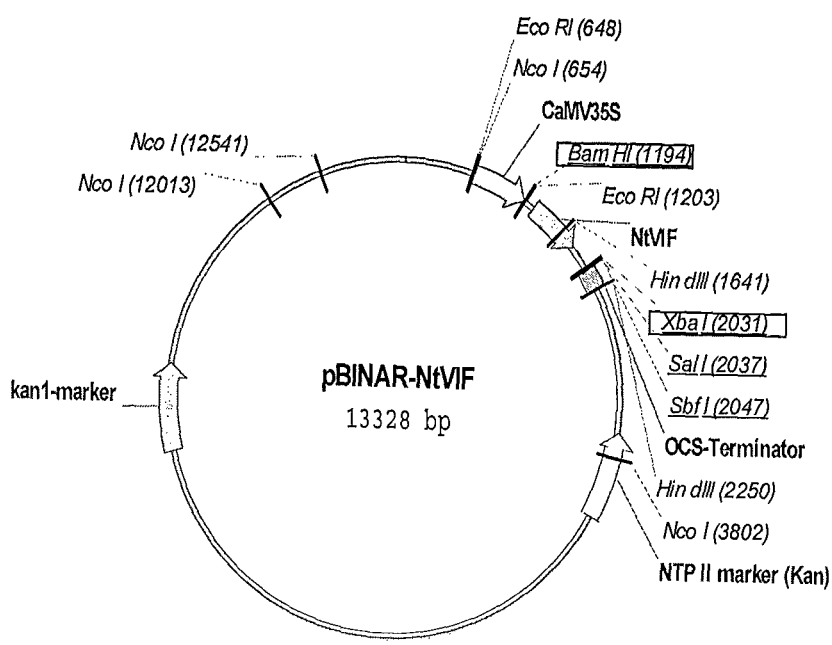

FIG. 2 shows the vector in which the invertase inhibitor from *Nicotiana tabacum* (SEQ ID NO: 1) was integrated (pBINAR-NtVIF).

Figure 3:
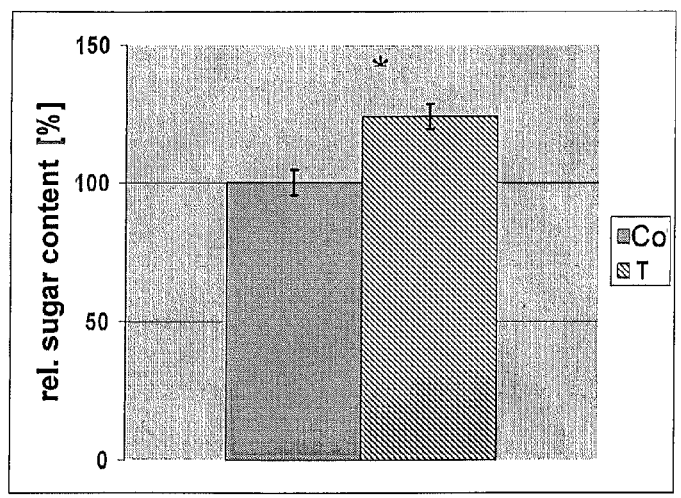

FIG. 3 shows the relative sucrose content in transgenic lines T (n=25) compared to non-transgenic controls Co (n=40). All plants were grown in the greenhouse in tubes and harvested 204 days after the planting of the seeds. The transgenic lines, with 24% higher sucrose content, differ significantly from the non-transgenic controls.

Figure 4:
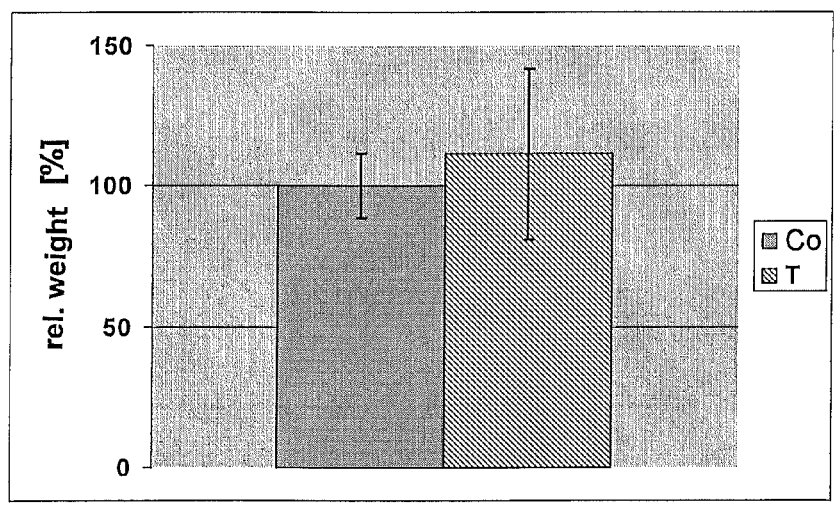

FIG. 4 shows the relative weight of the taproots of the plants according to FIG. 3. The weight of the taproots of the transgenic lines does not in this case differ from that of the control beets. Thus, the transgenic lines have a higher sucrose content compared to non-transgenic controls, and are not significantly modified in beet weight. The negative relationship between sucrose content and beet yield is broken in this case.

EXAMPLE OF USING A HETEROLOGOUS NUCLEIC ACID

At the restriction sites BamHI (1194) and XbaI (2031) a selected cDNA coding for an invertase inhibitor from *Nicotiana tabacum* with a length of 811 bp (SEQ ID NO 1) was integrated into the vector pBINAR so that plasmid pBINAR-NtVIF resulted.

The transformation of sugar beet was accomplished according to Lindsey et al. (1991). The transgenicity of the plants was checked by PCR. After regeneration, the transformants were grown and fertilized in the greenhouse for production of seeds.

The seed obtained by self fertilization of the selected transgenic lines and non-transgenic controls was sown or planted in early March, and the seedlings were separated in mid-March. The cultivation was carried out in the greenhouse in tubes (19×100 cm) at a temperature of ~16° C. and light intensity of 6 Klux and a light period of 18 hours. The tubes contained potting soil type FE 340 (Fruhsdorfer), seed compost LAT Terra P8 and 5 g Triabon. Every week the plants were fertilized with Kamasol 3-4‰ and treated against mildew and aphids. 204 days after the planting the beets were harvested, trimmed, washed, weighed and processed with a single beet grinder. The brei was frozen directly at −20° C.

SUCROSE DETERMINATION 26 g of sugar beet brei were extracted with 177 ml extraction solution (3 g of aluminum sulfate in 1000 ml ultrapure water) for 5 minutes at room temperature with stirring. The mixture was filtered through a 240 mm round filter and then diluted with ultrapure water 1:10. About 1.5 ml dilution filtrate was transferred into glass vials for HPLC analysis. 10 μl of the dilution filtrate were analyzed in a P1100 HPLC system from Agilent Technologies with a RI detector on a Merck Lichrocart 250-3 column (Lichrospher 100 NH2 (5 microns) Cat. No. 1.50834), in a mobile phase of 70% acetonitrile (v/v acetonitrile 70, water 30) and a flow rate of 0.8 ml/min. The HPLC-determined value gives sucrose in μg/ml and again was converted to % sucrose in relation to the beet fresh weight taking into consideration the dilution factor. For external calibration standard solutions of 100 mg sucrose/ml water, 500 mg sucrose/ml of water and 5000 mg sucrose/ml of water were used.

REFERENCES

Campbell, L. G., and Core, J. J. (1983). Relationship among components of yield and quality of sugarbeets. J. Am. Soc. Sugar Beet Technol. 22, 135-145.

Gonzales, M.-C., Roitsch, T., Cejudo, F. (2005). Circadian and developmental regulation of vacuolar invertase expression in petioles of sugar beet plants. Planta 222 (2) 386-395

Hoffmann, C., (2006). Sugar beet as raw material—the technical quality as a prerequisite for efficient processing. ISBN 978-3-93033-87-5.

Hoffmann, C., and Maerlaender, B., (2002). Genetic progress in yield and quality of sugar beet. Zuck Erind. 127, 425-429.

Lindsey, K., Gallois, P., Eady, C., (1991). Regeneration and transformation of sugar beet by *Agrobacterium tumefaciens*. Plant Tissue Culture Manual B7: 1-13, Kluwer Academic Publisher.

Milford, G. F. J., (1973). The growth and development of the storage root of sugar beet. Ann. Appl. Biol 75, 427-438.

Pressey, R., (1968). Invertase inhibitor from red beet, sugar beet and sweet potato roots. Plant Physiol., 43, 1430-1434.

Pressey, R., (1994). Invertase inhibitor in tomato fruit. Phytochemistry, 36, 543-546.

Rausch T., Greiner, S., (2004). Plant protein inhibitors of invertases. Biochimica et Biophysica Acta, 1696, 253-261.

Rosenkranz, H., Vogel, M., Greiner, S., Rausch, T., (2001). In wounded sugar beet (*Beta vulgaris* L.) tap-root, hexose accumulation correlates with the induction of a vacuolar invertase isoform. J Exp Bot, 52 (365), 2381-2385th Sambrook, J., Fritsch, E. F., and Maniatis, T., (1989). In Molecular Cloning, A Laboratory Manual (Cold Spring Harbor Laboratory Press, New York).

Schwimmer, S., Makower, R. U., Rorem, E. S., (1961). Invertase and invertase inhibitor in potato. Plant Physiol., 36, 313-316.

Sturm, A., (1999). Invertase. Primary structures, functions, and roles in plant development and sucrose partitioning. Plant Physiology 121, 1-7.

Sturm, A., Chrispeels, M. J., (1990). cDNA cloning of carrot extracellular beta-fructosidase and expression is in response to wounding and bacterial infection. Plant Cell 2, 1107-1119th Weil, M., Kraus Grill, S., Schuster, A., Rausch, T., (1994). A 17-kDa Nicotiana tabacum cell-wall peptide acts as in-vitro inhibitor of the cell-wall isoform of acid Invertase. Planta, 193, 438-445.

The invention claimed is:

1. A method to form a sucrose storage organ of a sugar beet or a sugarcane in which the sucrose concentration is increased relative to the sucrose concentration of an unchanged control sucrose storage organ of the same genotype at the stage of harvest, the method comprising
   a) introducing a nucleic acid sequence comprising SEQ ID NO: 2, or a nucleic acid sequence able to hybridize under stringent conditions with a sequence complementary to the sequence SEQ ID NO: 2 in a sugar beet or sugar cane cell, said nucleic acid encoding a polypeptide for reducing the enzymatic activity of an invertase, wherein said stringent conditions are hybridization in 4×SSC at 65° C. followed by repeated washing in 0.1×SSC at 65° C. for a total of about one hour,
   b) regenerating a primary transformant sugar beet or sugar cane plant comprising said nucleic acid from the transformed cell of step a);
   c) growing said primary transformant plant to produce transgenic seed;
   d) cultivating said transgenic seed to produce a progeny plant, whereby a sucrose storage organ of said progeny plant is formed in which the sucrose concentration, compared with the sucrose concentration of a non-genetically-modified control sucrose storage organ of the same genotype, is increased at harvest of said sucrose storage organs and non-genetically-modified storage organs, and wherein the sucrose concentration of said storage organ is not negatively correlated with the sucrose storage organ yield, or the increase in sucrose concentration by X percentage points leads to a reduced sucrose storage organ yield and the reduction of the sucrose storage organ yield is a maximum of 5 X percent.

2. The method of claim 1, wherein the nucleic acid sequence comprises a sequence according to SEQ ID NO: 2.

3. The method of claim 1, wherein the nucleic acid sequence comprises said nucleic acid sequence able to hybridize under stringent conditions with a sequence complementary to the sequence SEQ ID NO: 2.

4. A method for agricultural cultivation of sugar beet and sugar cane, the method comprising cultivating a transgenic sugar beet or sugar cane plant transformed with a nucleic acid sequence comprising SEQ ID NO: 2, or a nucleic acid sequence able to hybridize under stringent conditions with a sequence complementary to the sequence SEQ ID NO: 2, wherein said stringent conditions are hybridization in 4×SSC at 65° C. followed by repeated washing in 0.1×SSC at 65° C. for a total of about one hour, said nucleic acid encoding a polypeptide for reducing the enzymatic activity of an invertase, and said transgenic sugar beet or sugar cane plant is a progeny of a primary transformant grown from seed, whereby a sucrose storage organ is formed in which the sucrose concentration, compared with the sucrose concentration of a non-genetically-modified control sucrose storage organ of the same genotype, is increased at harvest of the transgenic and non-genetically modified plants, and wherein the sucrose concentration of the sucrose storage organ is not negatively correlated with the sucrose storage organ yield, or the increase in sucrose concentration by X percentage points leads to a reduced sucrose storage organ yield and the reduction of sucrose storage organ yield is a maximum of 5 X percent.

5. The method of claim 4, wherein the nucleic acid sequence comprises a sequence according to SEQ ID NO: 2.

6. The method of claim 4, wherein the nucleic acid sequence comprises said nucleic acid sequence able to hybridize under stringent conditions with a sequence complementary to the sequence SEQ ID NO: 2.

* * * * *